(12) United States Patent
Moros et al.

(10) Patent No.: US 7,723,346 B2
(45) Date of Patent: *May 25, 2010

(54) NON-SEDATING BARBITURATE COMPOUNDS AS NEUROPROTECTIVE AGENTS

(75) Inventors: Daniel A. Moros, Larchmont, NY (US); Barrie Levitt, Mamaroneck, NY (US); Avraham Yacobi, Englewood, NJ (US)

(73) Assignee: Taro Pharmaceutical Industries Ltd., Haifa Bay (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/355,336

(22) Filed: Feb. 16, 2006

(65) Prior Publication Data

US 2006/0205747 A1 Sep. 14, 2006

Related U.S. Application Data

(63) Continuation of application No. 10/865,428, filed on Jun. 10, 2004, which is a continuation of application No. 10/333,957, filed as application No. PCT/US01/23420 on Jul. 26, 2001, now Pat. No. 6,756,379.

(60) Provisional application No. 60/221,672, filed on Jul. 26, 2000.

(51) Int. Cl.
*A61K 31/515* (2006.01)
*C07D 239/62* (2006.01)
*C07D 239/64* (2006.01)

(52) U.S. Cl. .................................. 514/270; 544/305
(58) Field of Classification Search .................. None
See application file for complete search history.

(56) References Cited

U.S. PATENT DOCUMENTS

| | | | |
|---|---|---|---|
| 1,960,170 A | 5/1934 | Schnider | |
| 2,673,205 A | 3/1954 | Hoffmann et al. | |
| 3,679,683 A | 7/1972 | Gorbaty | |
| 3,711,607 A | 1/1973 | Vida et al. | |
| 3,900,475 A | 8/1975 | Vida et al. | |
| 3,904,627 A | 9/1975 | Vida et al. | |
| 3,919,427 A | 11/1975 | Vida et al. | |
| 3,930,006 A | 12/1975 | Wiggins et al. | |
| 3,948,896 A | 4/1976 | Vida | |
| 4,029,662 A | 6/1977 | Vida | |
| 4,046,894 A | 9/1977 | Samour et al. | |
| 4,060,528 A | 11/1977 | Janssen et al. | |
| 4,260,769 A | 4/1981 | Stella et al. | |
| 4,578,503 A | 3/1986 | Ishikawa et al. | |
| 4,628,056 A | 12/1986 | Levitt et al. | |
| 4,631,294 A | 12/1986 | Barsan | |
| 4,833,148 A | 5/1989 | Olney et al. | |
| 4,894,459 A | 1/1990 | Bod et al. | |
| 4,914,226 A | 4/1990 | Di Trapani et al. | |
| 5,120,850 A | 6/1992 | Bod et al. | |
| 5,128,477 A | 7/1992 | Bod et al. | |
| 5,456,851 A | 10/1995 | Liu et al. | |
| 5,474,990 A | 12/1995 | Olney et al. | |
| 5,750,766 A | 5/1998 | Krummel et al. | |
| 5,756,815 A | 5/1998 | Knell | |
| 5,808,066 A | 9/1998 | Krummel et al. | |
| 5,985,856 A | 11/1999 | Stella et al. | |
| 6,051,737 A | 4/2000 | Kim et al. | |
| 6,093,820 A | 7/2000 | Gutman et al. | |
| 6,156,925 A | 12/2000 | Meyer et al. | |
| 6,184,238 B1 | 2/2001 | Takano et al. | |
| 6,262,067 B1 | 7/2001 | Allen et al. | |
| 6,281,207 B1 | 8/2001 | Richter et al. | |
| 6,372,757 B1 | 4/2002 | Johns et al. | |
| 6,638,528 B1 | 10/2003 | Kanios | |
| 6,664,262 B2 | 12/2003 | Gutman et al. | |
| 6,756,379 B2 * | 6/2004 | Moros et al. ............... | 514/270 |
| 6,906,079 B2 | 6/2005 | Gutman et al. | |
| 6,939,873 B2 * | 9/2005 | Gutman et al. ............ | 514/270 |
| RE38,934 E | 1/2006 | Gutman et al. | |
| 7,064,205 B2 | 6/2006 | Gutman et al. | |
| 7,166,610 B2 * | 1/2007 | Moros ....................... | 514/270 |
| 7,227,021 B2 | 6/2007 | Gutman et al. | |
| 2003/0018080 A1 | 1/2003 | Gutman et al. | |

(Continued)

FOREIGN PATENT DOCUMENTS

DE 946 804 8/1956

(Continued)

OTHER PUBLICATIONS

Remington: The Science and Practice of Pharmacy, 20th edition; Published 2000 by Lippincott Williams and Wilkins, Edited by Daniel Limmer, pp. 317-322, 704-714, 858-863.*

(Continued)

*Primary Examiner*—Shaojia Anna Jiang
*Assistant Examiner*—Eric S Olson
(74) *Attorney, Agent, or Firm*—Venable LLP; Michael A. Gollin; Zayd Alathari

(57) ABSTRACT

Methods of providing neuroprotection are disclosed comprising administering a non-sedative barbiturate compound in an amount sufficient to achieve neuroprotection in a mammalian subject. Preferred compounds are in the family of diphenylbarbituric acid and analogs. Preferred doses for a neuroprotective effect exceed the dosage of a corresponding sedative barbiturate without sedative side-effects such as anesthesia and death.

27 Claims, No Drawings

U.S. PATENT DOCUMENTS

| | | | |
|---|---|---|---|
| 2003/0153589 A1 | 8/2003 | Moros et al. | |
| 2003/0187005 A1 | 10/2003 | Gutman et al. | |
| 2004/0167358 A1 | 8/2004 | Gutman et al. | |
| 2004/0186120 A1 | 9/2004 | Moros | |
| 2004/0224947 A1* | 11/2004 | Moros et al. | 514/228.8 |
| 2006/0004031 A1 | 1/2006 | Gutman et al. | |
| 2006/0035915 A1* | 2/2006 | Gutman et al. | 514/270 |
| 2006/0122208 A1* | 6/2006 | Gutman et al. | 514/270 |
| 2006/0258864 A1 | 11/2006 | Gutman et al. | |
| 2007/0072886 A1* | 3/2007 | Moros | 514/270 |
| 2007/0167624 A1 | 7/2007 | Gutman et al. | |

FOREIGN PATENT DOCUMENTS

| | | |
|---|---|---|
| DE | 11 00 639 | 3/1961 |
| DE | 11 03 339 | 3/1961 |
| DE | 1939787 | 2/1970 |
| DE | 2622981 A1 | 12/1977 |
| DE | 4028040 A1 | 3/1992 |
| EP | 726252 A1 | 8/1996 |
| EP | 726252 B1 | 8/1996 |
| EP | 1 083 172 A1 | 3/2001 |
| GB | 966098 | 8/1959 |
| WO | WO-99/18084 | 4/1999 |
| WO | WO 01/39779 | 6/2001 |
| WO | WO-01/79185 A1 | 10/2001 |
| WO | WO-02/07729 A1 | 1/2002 |
| WO | WO 03/063872 | 8/2003 |
| WO | WO 2004/052350 | 6/2004 |
| WO | WO 2006/003651 | 1/2006 |
| WO | WO 2006/026095 | 3/2006 |

OTHER PUBLICATIONS

Jax® Mice Literature, "Ask the Vet" No. 499 Published online in fall. 2005 at http://jaxmice.jax.org/library/notes/499c.html.*

Berge et al., "Pharmaceutical Salts" Journal of Pharmaceutical Sciences (1977) vol. 66, No. 1, pp. 1-19.*

Merriam-Webster's Collegiate Dictionary, Tenth Edition, published 1998 by Merriam-Webster, Incorporated, pp. 924 and 935.*

The Merck Manual of Diagnosis and Therapy, Seventeenth Edition, Published 1999 by Merck Research Laboratories, pp. 1421-1425.*

Bertram et al., "Phenobarbital is superior to phenytoin as an antiepileptic, neuroprotectant and antjepileptogenic agent in a rat model of status epilepticus and chronic limbic epilepsy," Epilepsia, vol. 37, No. Suppl. 5, p. 140 (1996); and Annual Meeting of the American Epilepsy Society, San Francisco, CA, USA, Dec. 7-10, 1996.

Shapiro, Barbiturates in Brain Ischaemia, British Journal of Anaesthesia, BJM Publishing Group London, Great Britain vol. 57, No. 1, Jan. 1985, pp. 82-95.

Swanson et al., "Barbiturates Impair astrocyte glutamate uptake," GLIA, Dec. 1998, vol. 34; No. 4, Dec. 1998, pp. 365-371.

Piatt, et al., "High dose barbiturate therapy in neurosurgery and Intensive care," Neurosurgery, vol. 15, No. 3, Sep. 1984, pp. 427-444.

Thacker et al., "Method for the Determination of 5,5-Diphenylbarbituric Acid and Separation from 1,3-Dimethoxymethyl-5,5-Diphenylbarbituric Acid in Plasma by High Performance Liquid Chromatography," J. Chromatography B, 710:149-155 (1998).

Raines et al., "Conversion of Dimethoxymethyl-Diphenylbarbituric Acid (DMMDPB) to Diphenylbarbituric Acid (DPB) in the Dog," The FASEB J., 13(4):A475, Abstract 394.2 (1999).

Raines et al., "The Effects of 5,5-Diphenylbarbituric Acid on Experimental Seizures in Rats: Correlation between Plasma and Brain Concentrations and Anticonvulsant Activity," Epilepsia, 16:575-581 (1975).

Raines et al., "A Comparison of the Anticonvulsant, Neurotoxic and Lethal Effects of Diphenylbarbituric Acid Phenobarbital and Diphenylhydantoin in the Mouse," J. Pharmacology and Experimental Therapeutics, 186(2):315-322 (1973).

Tagmann et al., Helv. Chim. Acta 35, 1541-1549 (1952).

Salmon-Legagneur et al., "Sur les acides a-phényl α-alcoyl (ou phénoalcoyl) glutariques", Comptes Rendus de l'Académie des Sciences, (Mar. 3, 1952) p. 1 060.

Salmon-Legagneur et al., "Recherches dans la série des diacides αα-disubstitués et de leurs dérivés. III. Les acides α-pheénol α-alcoyl (ou phénoalcoyl) glutariques et leurs principaux dérivés", Bull. Soc. Chim. France (1953) p. 70.

The Merck Index, 10th Ed., (Merck & Co., Inc., Rahway, NJ) (1983) p. 544 (entry 3697).

Casara et al., "Synthesis of acid stable fluorinated acyclonucleosides as potential antiviral agents," Tetrahedron Letters, 32(31) (1991), pp. 3823-3826.

Masuda et al., "Relationships Between Plasma Concentrations of Diphenylhydantoin, Phenobarbital, Carbamazepine, and 3-Sulfamoylmethyl- 1, 2-Benzisoxazole (AD-810), a New Anticonvulsant Agent, and Their Anticonvulsant or Neurotoxic Effects in Experimental Animals", Epilepsia, 20, pp. 623-633, (1979).

Bhardwaj et al., "Pentobarbital inhibits extracellular release of dopamine in the ischemic striatum", Journal of Neural Transmission [Gen Sect], 82, pp. 111-117, (1990).

McElvain, "5,5-Diphenylbarbituric Acid", 57, pp. 1303-1304, (1935).

Gesson et al., "A practical method for N-alkylation of succinimide and glutarimide", Bull Soc. Chim. Fr. 129, pp. 227-231, (1992).

Kamata et al., "Studies of Antitumor-Active 5-Fluorouracil Derivatives I Synthesis of N-Phthalidyl 5-Fluoroumcil Derivatives", Chem. Phann. Bull, 33 (8), pp. 3160-3175, (1985).

Samour et al., "Anticonvulsants, 1. Alkoxymethyl Derivatives of Barbiturates and Diphenylhydantoin", Journal of Medicinal Chemistry, 14 (3), pp. 187-189, (1971).

Raines et al., "Differential Selectivity of Several Barbiturates on Experimental Seizures and Neurotoxicity in the Mouse", Epilepsia, 20, pp. 105-113, (1979).

Loudon, "Organic Chemistry", Addison-Wesley (1984), pp. 617, 721-722, 1061-1064, 1086-1088, 1194.

Corkill et al., Surg. Neural., pp. 147-149 (1976).

Hoff et al., Stroke, 6, pp. 28-33, (1975).

Levy and Brierley, "Delayed pentobarbital administration limits ischemia brain damage in gerbils", Annals of Neurology, 5(1), pp. 59-64, (1979).

Lightfoote et al., Stroke, 8, pp. 627-628, (1977).

Pulsinelli and Brierley, "A new model of bilateral hemispheric ischemia in the unanesthetized rat", Stroke, May-June 10(3), May pp. 267-272, (1979).

Raines et al., Epilepsia 1996, 37:Suppl. 5.

Ginsberg, "Animal Models of Global and Focal Cerebral Ischemia," Chapter 34 in Welsh KMA et al., *Primer on Cerebrovascular Diseases*, Academic Press, New York (1997).

Miller, ed., "Stroke Therapy: Basic, preclinical, and clinical directions", Wiley (1999).

Brint et al., "Focal brain ischemia in the rat: Methods for reproducible neocortical infarction using tandem occlusion of the distal middle cerebral and ipsilateral common carotid arteries", J. Cerebral Blood Flow Metab., 8, pp. 474-485, (1988).

Garcia et al., "Neurological deficit and extent of neuronal necrosis attributable to middle cerebral artery occlusion in rats. Statistical validation", Stroke, 26(4), pp. 627-634, (1995).

Garcia et al., "Neuronal necrosis after middle cerebral artery occlusion in Wistar rats progresses at different time intervals in the caudoputamen and the cortex", Stroke, 26(4), 636-643 (1995).

Pulsinelli et al., "Temporal profile of neuronal damage in a model of transient forebrain ischemia", Annals of Neurology, May 11(5),491-498,(1982).

Raines et al., J. Exp. Biol. (Abstracts) Abstract No. 895 (Apr. 14-17, 1996).

Foye, "Principles of Medicinal Chemistry," 3rd ed. (1990) pp. 164, 179.

Karger et al., "Methoxymethyl Methanesulfonate, A Novel Active Oxyalkylating Agent," J. Am. Chem. Soc., 91:5663 (1969).

Sircar, J. Chem. Soc. (1927) 1252-1256.

Gao et al., "Physical Chemical Stability of Warfarin Sodium," AAPS Pharmasci (2001) 3(1) Article 3.

Appendix 1 of U.S. Appl. No. 60/352,273, filed Jan. 30, 2002: Chemical Derivative Chart (total of 8 pages).
Appendix 2 of U.S. Appl. No. 60/352,273, filed Jan. 30, 2002: References to Chemical Derivatives (total of 3 pages).
Appendix 3 of U.S. Appl. No. 60/352,273, filed Jan. 30, 2002: CANCERLIT . . . (total of 9 pages).
Appendix 3 of U.S. Appl. No. 60/352,273, filed Jan. 30, 2002: PubMed search results printout of Jan. 15, 2002 (total of 7 pages).
Appendix 3 of U.S. Appl. No. 60/352,273, filed Jan. 30, 2002: MEDLINEplus of Jan. 15, 2002: Barbiturates (Systemic) (total of printout 14 pages).
PubMed search results printout of Dec. 27, 2002 (total of 3 pages).
Pharmaceutical Chemistry, Mar. 7, 1981.
Office Action issued by the USPTO on Nov. 1, 2007 for U.S. Appl. No. 10/865,428.
Office Action issued by the USPTO on Sep. 28, 2007 for U.S. Appl. No. 11/355,339.
Office Action issued by the USPTO on Dec. 5, 2007 for U.S. Appl. No. 11/201,024.
Office Action issued by the USPTO on Jan. 11, 2008 for U.S. Appl. No. 11/727,557.
International Search Report issued in PCT Application No. PCT/US04/041138, mailed on Aug. 10, 2005.
Written Opinion issued in PCT Application No. PCT/US04/041138, mailed on Aug. 10, 2005.
Zavadil et al., Effects of Diphenylbarbituric Acid on Neuromuscular and Spinal Cord Function in the Cat, Neuroscience Abstracts, p. 694 (1975).
Acta Neurol Scand., 1987:75:332-340, "Primidone and Propranolol in Essential Tremor: A Study Based on Quantitative Tremor Recording and Plasma Anticonvulsant Levels", P. Dietrichson, et al.
Aldrich Chemical Catalog, 1990-1991, p. 303.
Alles et al. "Comparative central depressant actions of some 5-phenyl-5-alky barbituric acids" (J. Pharmacol Exp. Ther.) 1947, 89: 356-367.
Arch Otolaryngol, vol. 110, Jun. 1984, pp. 394-397, "Spastic Dysphonia and Essential (Voice) Tremor Treated With Primidone", David E. Hartman, et al.
Archives of Neurology, Apr. 1999, vol. 56, No. 4: 475-480, Alexandre Gironell, et al., "A Randomized Placebo-Controlled Comparative Trial of Gabapentin and Propranolol in Essential Tremor".
Bashir, K. et al.: "Clozapine for the control of hemiballismus," Clinical Neuropharmacology, vol. 17, No. 5, 1994, pp. 477-480, XP009032005.
Barnes, Harry M. and McElvain, S. M. "For Further Observations on the Condensation of Benzene with Alloxan" (J. Am. Chem. Soc.) Jul.-Dec. 1937, 59: 2348-2351.
Baumel et al. "Metabolism and anticonvulsant properties of primidone in the rat" (J. Pharmacol Exp. Ther.) 1973, 186: 305-314.
Boron Tribromide, Encyclopedia of Reagents for Organic Synthesis edited by Leo Pacquette, pp. 1-9, 2003.
Breimer et al. "Pharmacokinetics and relative bioavailbility of heptabarbital and heptabarbital sodium after oral administration to man" (Eur. J. Clin. Pharmacology) 1975, 9: 169-178.
C.D. Marsden, Origins of Normal and Pathological Tremor in Movement Disorders: Tremor. Eds. L.J. Findley and R. Capildeo, New York, Oxford University Press, 1984, pp. 37-84 "Origins of Normal and Pathological Tremor".
Clinical Neuropharmacology vol. 10, No. 4, 1987, pp. 342-350, Essential Tremor Variants: Effect of Treatment, William C. Koller, et al.
Clinical Neuropharmacology, vol. 13, No. 1, 1990, pp. 67-76, "Primidone in the Long-Term Treatment of Essential Tremor: A Prospective Study with Computerized Quantitative Analysis", Enrico Sasso, et al.
Clinical Neuropharmacology, vol. 13, No. 3, 1990, pp. 210-223, "Basic Mechanism of Action of Drugs Used in the Treatment of Essential Tremor", Xiao-Ming Guan, et al.
Clinician, May 2001, vol. 19, No. 2, pp. 1-15, "Essential Tremor: A Practical Guide to Evaluation, Diagnosis, and Treatment".
Craig et al. "Metabolism and anticonvulsant properties of mephobarbital and phenobarbital in rats" (J. Pharmacol Exp. Ther.) 1971, 176: 35-41.
Dox et al "5,5-Diarylbarbituric Acids" (J. Chem. Soc.) 1923, 45: 1811-1816.
Fink et al. "Modification of maximal audiogenic and electroshock seizures in mice by psychopharmacologic drugs" (J. Pharmacol Exp. Ther.) 1959, 127: 318-324.
Gibaldi et al. "Pharmokinetics Second Ed." 2nd Ed Marcel Dekker, Inc. 1982.
Glazko, A.J. "Diphenylhydatoin" (Pharmacology) 1972, 8: 163-177.
Glazko et al. "Early adventures in drug metabolism: 2. The absorption of drugs" (Ther. Drug Monit.) 1987, 9: 180-89.
Goodman & Gilman's The Pharmacological Basis of Therapeutics, 9th Ed. Ch. 17, 361-396, William R. Hobbs et al., "Hypnotics and Sedatives; Ethanol".
Goodman & Gilman's "The Pharmacological Basis of Therapeutics 2001" p. 412-419, 10th Ed.
Hamann, M. et al.: "Effects of striatal injections of GABAA receptor agonists and antagonists in a genetic animal model of paroxysmal dystonia," European Journal of Pharmacology, vol. 443, No. 1-3, May 17, 2002, pp. 59-70, XP002284223.
Iadarola et al. "Comparison of the effects of diphenylbarbituric acid, phenobarbital, pentobarbital and secobarbital . . . " (J. Pharmacol Exp. Ther.) 1985, 232: 127-133.
International Search Report issued in PCT Application No. PCt/US03/39530, mailed on Jul. 7, 2004.
Journal of Neurology, Neurosurgery, and Psychiatry 1985;48:911-915, "Primidone in Essential Tremor of the Hands and Head: A Double Blind Controlled Clinical Study", Leslie J. Findley, et al.
Journal of Neurology, Neurosurgery, and Psychiatry 1986;49:64-68, "A Comparison of Primidone, Propranolol, and Placebo in Essential Tremor, Using Quantitative Analysis", W.P. Gorman, et al.
Knoefel et al. "The anticonvulsant action of diphenylhydatoin and some related compounds" (J. Pharmacol Exp. Ther.) 1942, 76: 194-201.
Mayo Clinic Proceedings, vol. 66, No. 10, Oct. 1991, pp. 991-997, Manfred D. Muenter, et al. "Treatment of Essential Tremor With Methazolamide".
McKeown et al. "Thermodynamic functions for dissociation of 5,5-disubstituted barbituric acids- their signficance in structure-reactivity . . . " (Ellis Horwood) 1986, 6: 80-89.
Merck Manual of Diagnosis and Therapy, Seventeenth Edition, Beers et al., ed., (1999), Chapter 179, pp. 1462-1473.
Merritt et al. "Experimental determination of anticonvulsive activity of chemical compounds" (Epilepsia) 1945, 3: 51-75.
Modern Pharmacology, 2nd Ed., 1986, Ch. 4, pp. 41-64, Theodore E. Gram "Metabolism of Drugs".
Movement Disorders 2, 1987, (22) 438-458, Leslie J. Findley, "The Pharmacology of Essential Tremor".
Movement Disorders, vol. 13, Suppl 3., pp. 90-100, 1998, Paul G. Wasielewski, et al. "Pharmacologic Treatment of Tremor".
Movement Disorders, vol. 16, No. 3, 2001 pp. 464-468, William C. Koller, et al. "Long Term Safety and Efficacy of Unilateral Deep Brain Stimulation of the Thalamus in Essential Tremor".
Movement Disorders, vol. 6, No. 1, 1991, pp. 65-68, "Quantitative Comparison of Barbiturates in Essential Hand and Head Tremor", Enrico Sasso, et al.
Neurology, 1985, 35:1784-1787, "Phenobarbitone in Essential Tremor", Leslie J. Findley, et al.
Neurology, 1986; 36:121-124, "Efficacy of Primidone in Essential Tremor", William C. Koller, et al.
Neurology, 1988, 38:808-810, "Double-Blind Comparison of Primidone and Phenobarbital in Essential Tremor"; Enrico Sasso, et al.
Neurology, Jun. 2000 vol. 54, Supp.I 4, S30-S38, William C. Koller et al., "Pharmacologic Treatment of Essential Tremor".
Neurology, Jun. 2000, vol. 54, Suppl 4, S8-S13, Leslie J. Findley, "Epidemiology and Genetics of Essential Tremor".
Nims et al. "Compartive pharmacodynamics of hepatic cytochrome P450 2B induction by 5,5-diphenyl- and 5,5-diethyl substituted . . . " (J. Pharmacol. Exp. Ther.) 1994, 270: 348-355.
Ondo, W. et al.: "Essential tremor. Treatment Options," CNS Drugs 1996 New Zealand, vol. 6, No. 3, 1996, pp. 178-191, XP009032012.

Parkinson's Disease and Movement Disorders, Urban & Schwarzenberg, Inc., 1988, 17: 225-234, Stanley Fahn, et al. "Clinical Rating Scale for Tremor".
Prankerd et al. "Physio-chemical properties of barbituric acid derivatives: IV. Solubilities of 5,5-disubstituted barbituric acids . . . " (Int. J. Pharmaceutics) 1994, 112: 1-15.
Raines et al., "Anticonvulsant properties of 5,5-diphenylbarbituric acid (DPB)" (Pharmacology) 1973, 32: 3246.
Raines et al. "Pre and postjunctional effects of diphenylhydantoin at the cat soleus neuromuscular junction" (J. Pharmacol Exp. Ther.) 1966, 153: 361-366.
Raines et al., Chemical Abstracts, 79:87539k, 1973.
Raines et al., Chemical Abstracts, 92:174402x, 1980.
Remington: The Science and Practice of Pharmacy, 20th Edition; Published 2000 by Lippincott Williams and Wilkins, Edited by Daniel Limmer, pp. 743-747.
Rev. Neurol., 2001, 32 (6): 520-524; I. Balas et al. "Talamotomia esterotaxica de la enfermedad de Parkinson y otros tipos de temblor. Experiencias de la actividad multiunitaria burst en el talamo basada en semimicroelectrodos". (English Abstract).
Serrano et al. "Intramuscular administration of diphenylhydantoin" Arch. Neurol., Oct. 1974, 31: 276-277.
Stavber et al., Chemical Abstracts, 99:157381s, 1983.
Sturfelt, G. et al.: Acute Effects of Barbiturates in Parkinson's Disease, "Acta Medica Scandinavica, Almqvist & Wiksell Periodical Co.;" Stockholm, SE, vo. 201, No. 1/2, 1977, pp. 75-76, XP000937405.
The New England Journal of Medicine, vol. 339, No. 16, Oct. 1998, pp. 1130-1143, Anthony E. Lang, et al. "Parkinson's Disease", Second of Two Parts.
The New England Journal of Medicine, vol. 345, No. 12, Sep. 2001 pp. 887-891, Elan D. Louis, "Essential Tremor".
Weinryb et al., Chemical Abstracts, 76:1206c, 1972.
Whittle et al. "Differential effect of sedative and anticonvulsant barbiturates on specific gaba binding to membrane prep . . . " (Bio. Pharmacology) 1982, 31: 2891-2895.
Yeh et al. "A comparison of numerical integrating algorithms by trapezoidal, lagrange, and spline approximations." (J. Pharmacokinet Biopharm) 1978, 6: 79.
Zavadil III, et al. "Diphenylbarbituric Acid" (Epilepsia) 1985, 26: 158-166.
European Search report issued in EP Application EP 05 29 0804, dated Jun. 16, 2005.
European Search report issued in EP Application EP 01 95 9195, dated Feb. 24, 2006.
MedlinePlus Medical Encyclopedia, Convulsions p. 1-4.
Office Action issued by the USPTO on Aug. 5, 2008 for U.S. Appl. No. 10/865,428.
Broderick et al., "Guidelines for the Management of Spontaneous Intracerebral Hemorrhage," Stroke, vol. 30, pp. 905-915, 1999.
IUPAC, Glossary of terms used in Medicinal Chemistry, pp. 1-10, 1998.
Office Action issued by the USPTO on Apr. 22, 2009 for U.S. Appl. No. 10/865,428.
Constantino et al., "Metabotropic glutamate receptors: targets for therapy of cerebral ischaemia," Expert Opinion on Therapeutic Drugs, vol. 5, pp. 669-683, 2001.
Office Action Issued by the USPTO on Mar. 24, 2009, for U.S. Appl. No. 11/169,044.
Office Action Issued by the USPTO on Mar. 6, 2009, for U.S. Appl. No. 11/355,339.
Office Action Issued by the USPTO on Apr. 20, 2009, for U.S. Appl. No. 11/201,024.
European Search report issued in EP Application No. 03 01 1817, completed Jul. 14, 2003.
European Search report issued in EP Application No. 03 73 5068, dated Feb. 28, 2006.
European Search report issued in EP Application No. 05 78 6192, dated Nov. 22, 2007.
International Search Report Issued in PCT Application No. PCT/US98/20665, mailed on Apr. 2, 1999.
International Search Report Issued in PCT Application No. PCT/US01/23420, mailed on Nov. 20, 2001.
International Search Report Issued in PCT Application No. PCT/US03/02638, mailed on Jun. 18, 2003.
International Search Report issued in PCT Application No. PCT/IL2005/000697, mailed on Oct. 13, 2006.
International Search Report issued in PCT Application No. PCT/US2005/028380, mailed on Dec. 8, 2006.
International Preliminary Examination Report issued in PCT Application No. PCT/US01/23420, completed on Feb. 23, 2003.
International Preliminary Examination Report issued in PCT Application No. PCT/US03/02638, completed on Oct. 31, 2003.
International Preliminary Examination Report issued in PCT Application No. PCT/US03/039530, completed on Mar. 10, 2005.
International Preliminary Report on Patentability issued in PCT Application No. PCT/IL2005/000697, issued on Jan. 9, 2007.
International Preliminary Report on Patentability issued in PCT Application No. PCT/US2005/028380, issued on Feb. 13, 2007.
Goodman & Gilman's The Pharmacological Basis of Therapeutics, 9th Ed., 373-380 (1996).
Kojima, Chem. Pharm. Bull. 21 (11): 2432-2437 (1973).
Kojima et al., J. Pharm Sci. 60: 1639-1641 (1971).
Malhotra, S. et al., "T-2000, a novel non-sedating barbiturate reduces infact size and improves neurologic functions following MCAO in the rat," Program No. 821.10. 2004 Abstract Viewer/Itinerary Planner. Washington, DC: Society for Neuroscience, 2004. Online.
Rekling Jens C., "Neuroprotective effects of anticonvulsants in rat hippocampal slice cultures exposed to oxygen/glucose deprivation", Neuroscience Letters, vol. 335, No. 3, Jan. 2, 2003, pp. 167-170.
Vida J. A. et al, "Anticonvulsants. IV. Metharbital and phenobarbital derivatives" Journal of Medicinal 1378-1381, (1973) vol. 16 No. 12 pp. 1378-1381.
Vida J. A. et al, "Anticonvulsants. III. Phenobarbital and mephobarbital derivatives", Journal of Medicinal Chemistry 1973, vol. 16, p. 602-605.
Werner W. et al., "Structure effect interactions in Mannich bases with and without nitrogen mustard groups and some reference compounds as potential immunosuppressive agents", retrieved from STN Database accession No. 85: 72035, Pharmazie 31(5) 282-7, 1976.
Selleri, R. et al., "N1, N3-Disubstituted barbituric acid derviates of ganglioplegic or curarelike action", retrieved from STN Database accession No. 1959:111820, Farmaco, Edizione Scientifica, 12, 3-14, 1957.
Casagrande, C. et al., "Synthesis and antiarrhythmic activity of 5,5-disubstituted-3-aminoalkylhydantoins and some heterocyclic and noncyclic analogs", retrieved from STN Database accession No. 1975:43261, Farmaco, Edizione Scientific, 29(10) 757-785, 1974.
Vida J. et al., "Anticonvulsants. 2. Acyloxymethyl and halomehtyl derivaitves of barbituric acid and diphenylhydantoin", Journal of Medicinal Chemistry, 14(3): p. 190-193, Mar. 1971.
Office Action Issued by the USPTO on Dec. 28, 2009, for U.S. Appl. No. 10/865,428.
Ukkola et al., "Epilepsy After Operative Treatment of Ruptured Cerebral Aneurysms," Acta Neurochirurgica, vol. 106, pp. 115-118, 1990.
Office Action Issued by the USPTO on Jul. 8, 2009, for U.S. Appl. No. 10/856,428.
Office Action Issued by the USPTO on Jun. 30, 2009, for U.S. Appl. No. 11/201,024.

* cited by examiner

US 7,723,346 B2

NON-SEDATING BARBITURATE COMPOUNDS AS NEUROPROTECTIVE AGENTS

This application is a continuation of U.S. patent application Ser. No. 10/865,428 filed Jun. 10, 2004 which is a continuation of U.S. patent application Ser. No. 10/333,957, filed Jan. 27, 2003, now U.S. Pat. No. 6,756,379 which claims the benefit under 35 U.S.C. §371 of PCT/US01/23420, filed Jul. 26, 2001 which claims priority under 35 U.S.C. §1.119(e) of Provisional Application Ser. No. 60/221,672, filed Jul. 26, 2000, the disclosures of which are incorporated by reference in their entireties herein.

BACKGROUND OF THE INVENTION

The invention relates to the use of non-sedating barbiturate compounds given in a manner and dosage effective to produce blood levels and brain levels of these drugs and/or their active metabolites sufficient to provide a neuroprotectant effect. In particular, the methods and formulations of the invention permit treatment of cerebral ischemia, head trauma and other acute neurologic injuries, and prevention of resulting neuronal damage.

Ischemia (stroke) is the third leading cause of death in the United States. When blood supply to the brain is reduced below a critical threshold, a cascade of biochemical events leads to irreversible damage to neurons and brain infarction. Research on treatment and prevention of ischemia is extensive but unfortunately it remains at a basic stage and no adequate therapies are yet in practice (10).

Barbiturates in high concentrations have been shown to be neuroprotective in cerebral ischemia in rodents and primates, to reduce the extent of ischemia brain infarction, and to prevent or lessen brain damage (1-4). One theory as to how barbiturates prevent neuronal injury in ischemia is that they inhibit the ischemia-induced uncontrolled release of neurotransmitters, which can attain high, neurotoxic concentrations that cause neuronal death (5).

The literature regarding the neuroprotective effects of anesthetic barbiturates is over two decades old, but the clinical use of barbiturates has been severely limited because of toxicity. The dosages and blood and brain levels necessary to confer neuroprotection are toxic and cause lethargy, stupor, and coma. Even higher doses that might be more effective are lethal (1-4, 6), making barbiturates unsuitable for treatment of ischemia (1). These toxic side effects establish a "functional ceiling" on dosage for barbiturates, and have discouraged further research into the use of anesthetic/sedative barbiturates to protect from ischemia.

Levitt et al., U.S. Pat. No. 4,628,056 describes non-sedating oxopyrimidine derivatives and their use as anticonvulsants, anti-anxiety and muscle relaxant agents. The literature does not suggest the use of such compounds as neuroprotectant agents. Indeed, even in published studies about using sedative barbiturates for neuroprotection there is no reference to non-sedating barbiturate compounds. It is generally believed that the anticonvulsant and neuroprotective effects of barbiturates are linked to their sedative/hypnotic effects. For example, Lightfoote et al. suggested that the protective effects of pentobarbital are due to the duration of the barbiturate-induced anesthesia (3). This viewpoint has been reinforced by biochemical studies at the cell receptor level that relate all these effects to action at the GABA receptor. Thus, the prior art teaches away from using sedative barbiturates for neuroprotection because of their toxicity, and also teaches away from using non-sedative barbiturates as neuroprotectants because they lack sedating or anesthetic properties.

SUMMARY OF THE INVENTION

In summary, the invention involves non-sedating barbiturates such as for example 1,3-dimethoxymethyl 5,5-diphenyl-barbituric acid (DMMDPB), 1-monomethoxymethyl 5,5-diphenylbarbituic acid (MMMDPB) and diphenyl-barbituric acid (DPB) and their precursors, derivatives and analogs, and their administration over a range of dosages that result in a range of blood levels and brain levels of these drugs and their metabolites making them useful as neuroprotectants. In particular, the invention is directed to the treatment of cerebral ischemia, head trauma and other acute neurologic injuries, using non-sedating barbiturates.

There are many circumstances where individuals at risk of cerebral ischemia are clearly identified in advance, for example: individuals undergoing cardiac surgery or carotid endarterectomy, and individuals with atrial fibrillation, transient ischemic attacks (TIAs), bacterial endocarditis, strokes, or subarachnoid hemorrhage due to a cerebral aneurysm. In such cases, a non-sedating barbiturate is used prophylactically in individuals at risk for ischemic damage. The drugs can also be used after an acute event. These compounds can be given in oral form as a tablet, capsule, liquid or via intravenous or other parental routes.

This invention succeeds where previous efforts to treat cerebral ischemic attack with barbiturates have failed. This invention solves a problem previously thought to be insoluble, that of toxic effects of neuroprotective dosages of barbiturates. The invention avoids the toxicity and sedative effects of barbiturates known in the prior art without loss of efficiency.

This invention satisfies a long-felt need for a non-toxic neuroprotectant, and is contrary to the teachings of the prior art regarding the inability of barbiturates to produce clinically meaningful neuroprotection. According to the invention, it is possible to separate the anticonvulsant and sedative effects of barbiturates, and neuroprotection correlates much better with the anticonvulsant rather than the sedative effect of barbiturates.

This invention differs from the prior art in the recognition of specific compounds, their modifications and dosages that are effective in neuroprotection but that were not previously recognized.

The present invention is a method for providing neuroprotection to a mammal, preferably a human. The method comprises administering to the mammal a non-sedating barbiturate in a dose effective to provide a neuroprotection effect. Non-sedating barbiturates for use in the invention include one or more selected from the group consisting of 1,3-dimethoxymethyl 5,5-diphenyl-barbituric acid (DMMDPB), 1-monomethoxymethyl 5,5-diphenylbarbituric acid (MMMDPB), and diphenyl barbituric acid (DPB). The precursors, derivatives and analogs of the foregoing compounds, as well as the salts of all the foregoing are also suitable for practicing the invention.

The effective neuroprotective dose of the non-sedative barbiturate preferably exceeds the coma-producing dose of a sedative barbiturate. Depending on the specific need of the mammal, the dose of the non-sedative barbiturate may exceed a dose that would be lethal with a sedative barbiturate. This unexpected and seemingly paradoxical effect of the present method is further reflected in the relative dosage levels that are possible with the methods of this invention.

Also, the neuroprotective dose of the non-sedative barbiturate exceeds the minimum anticonvulsant dosage of the barbiturate. In some embodiments of the present invention the effective dose of the non-sedative barbiturate is in the range of from about 2 times to about 5 times the anticonvulsant dosage. In yet other contexts where the need of the mammal requires, the effective dose of the non-sedative barbiturate is in the range of from about 5 times to about 10 times the anticonvulsant dosage of the non-sedative, or even higher so long as the dose is clinically acceptable.

Advantageously, the neuroprotective effect of the present methods can be used to mitigate the effect of cerebral ischemic. The non-sedating barbiturate can be administered orally, intravenously, transdermally, in combination with an adjuvant, or transpulmonarily by means of a particulate or aerosol inhalant. Moreover, within the scope of the invention, the non-sedating barbiturate can be administered preventively, prophylactically or therapeutically, at a clinically acceptable dose. The compound may be administered prophylactically before evident neuronal damage, or therapeutically after onset of neuronal damage. The neuroprotective effect diminishes, or protects the subject from, neuronal damage caused by head trauma or cerebral ischemia. The compound may be administered in conjunction with cardiac surgery or carotid endarterectomy. The mammalian subject may have or be at risk for atrial fibrillation, a transient ischemic attack (TIA), bacterial endocarditis, a stroke, head trauma, or subarachnoid hemorrhage.

Typically, to achieve neuroprotection the non-sedating barbiturate is administered in a dose sufficient to obtain blood concentrations of at least about 30 μg/ml of barbiturate, preferably at least about 100 μg/ml, more preferably at least about 250 μg/ml, and possibly as high as 200-300 μg/ml, or even higher. In contrast, the reported therapeutic range for phenobarbital is lower, 10-30 μg/ml blood levels (6). Thus, preferred ranges are at or above about 25, 30, 50, 75, 100, 200, 250, or 300 μg/ml.

The invention includes a pharmaceutical composition comprising a non-sedative barbiturate administered in an amount effective to have a neuroprotectant effect. Preferably, the non-sedative barbiturate is administered in oral doses in the range of from about 25 to about 1,500 mg/kg/day body weight. Preferably the dose is greater than about 25 mg/kg/day, or greater than about 100 mg/kg/day, or greater than 250 mg/kg/day. A preferred dose is one that is pharmacologically equivalent to a dose of about 1000 mg/kg/day in the rat. Thus, dosage forms may be sufficient individually or in multiple doses to provide a dose equal to or above about 15, 20, 25, 50, 70, 100, 250, 500, 1000, or 1500 mg/kg body weight per day.

In human trials it has been unexpectedly found that DMMDPB, one of the neuroprotectant compounds, is much better absorbed in humans than in rats or dogs. It has further been found that the half life of DMMDPB, as well as the half life of MMMDPB and DPB are greater than the half-lives found in rats or dogs. Specifically, with dosages of 20 mg/kg/day, the half-lives of DMMDPB, MMMDPB, and DPB are approximately 20 hrs, 20 hrs, and 50 hrs respectively after a two week exposure in humans. Similarly, the maximum concentration (Cmax) of the drug in the blood following 7 days of dosing in the range of 20 mg/kg/day are 1.2 μg/ml, 36 μg/ml and 43 μg/ml respectively.

The unexpectedly high absorption and prolonged half-life in humans makes it possible to achieve substantial blood levels with lower than expected oral dosages. Thus, for example, it is possible to obtain total barbiturate blood levels (i.e., DMMDPB+MMMDPB+DPB)>53 μg/ml with dosages of about 15 mg/kg/day; and total barbiturate levels >72 μg/ml with dosages in the range of 20 mg/kg/day. Blood levels of non-sedating barbiturates greater than 100 μg/ml are achieved with dosages between about 40 and about 100 mg/kg/day, and are within the scope of the invention. With parenteral administration of non-sedating barbiturates, similar blood concentrations are obtained with daily dosages of less than 25 mg/kg/day. However, first day loading dosages may still need initial dosages of greater than 25 mg/kg.

The invention provides an article of manufacture comprising a container comprising a pharmaceutical composition and a label with indications for use as a neuroprotectant, the pharmaceutical composition comprising a non-sedating barbiturate compound in an amount effective for neuroprotection upon administration to a subject in need of neuroprotection; and a pharmaceutically acceptable carrier or excipient.

Another embodiment is a method for providing neuroprotection comprising (a) diagnosing a patient's need for cerebral neuroprotection, (b) selecting a non-sedative barbiturate, and (c) providing to the patient a dose of the non-sedative barbiturate sufficient to raise the concentration in the patient's brain to a level effective to provide neuroprotection.

Further objectives and advantages will become apparent from a consideration of the description and examples.

DETAILED DESCRIPTION OF THE PREFERRED EMBODIMENTS

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose. Each reference cited here is incorporated by reference as if each were individually incorporated by reference.

The term "non-sedative barbiturate" encompasses the family of 5,5-diphenyl barbituric acid anticonvulsant compounds described in Levitt et al., U.S. Pat. No. 4,628,056, and metabolic precursors and metabolites, and derivatives and structural analogs (including addition salts thereof) having a non-sedative neuroprotectant activity. Other barbituric acid derivatives that are non-sedating are also within the scope of the invention.

Derivatives, precursors, and analogs of barbituric acid include barbituric acids of the formula:

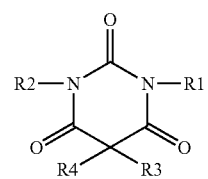

wherein one or more nitrogen is substituted with lower alkyl, or a lower alkoxy substituted lower alkyl group; or at least one of $R^1$ and $R^2$, together with the nitrogen, forms a carbamate, an amide, or an acetal of the formamide derivative, i.e. $R^1$ or $R^2$ is $CO_2R$, COR or $CH(OR)_2$. Methylether groups are preferred $R^1$ and $R^2$ groups and methoxymethyl is more preferred. Methyl is also a preferred value for $R^1$ and/or $R^2$. Other derivatives of barbituric acids according to the invention are carbamates, amides and acetals where one or both of $R^1$ and $R^2$ is $CH_2OR^5$, wherein $R^5$ is lower alkyl, alkylaryl or benzyl; $CO_2R^6$, wherein $R^6$ is lower alkyl or aryl; $COR^7$, wherein $R^7$ is hydrogen, lower alkyl or aryl; or $CH(OR^8)_2$, wherein $R^8$ is a lower alkyl group.

Preferred values for $R^3$ and $R^4$ are aryl, phenyl, phenyl substituted with a halogen or lower alkyl group, benzyl, benzyl wherein the aromatic ring is substituted with a halogen or lower alkyl group, lower alkyl or lower alkyl substituted with an aromatic moiety. Aryl represents any carbocyclic ring, such as phenyl, naphthyl and higher analogues, as well as heteroaromatic rings substituted with one or more heteroatoms such as sulfur, oxygen and nitrogen. According to the invention, nonsedating barbituric acid derivatives are those where at least one of $R^3$ and $R^4$ is an aromatic ring or an aromatic ring containing moiety e.g. aryl, phenyl, substituted phenyl, benzyl, substituted benzyl or arylalkyl. Preferred substituents on the aromatic rings are methyl, ethyl, and fluorine. Phenyl and substituted phenyl are preferred for $R^3$ and $R^4$. Embodiments where $R^3$ and $R^4$ are both phenyl are most preferred.

In preferred compounds, one of $R^1$ and $R^2$ is hydrogen, or one or both of $R^1$ and $R^2$ is methyl or alkoxymethyl, preferably methoxymethyl. At least one and preferably both of $R^3$ and $R^4$ is preferably phenyl or substituted phenyl, tolyl, fluorophenyl, ethylphenyl.

As can be readily understood, salts of the above compounds are also contemplated, including organic salts, such as acid addition and base addition salts.

In order to fall within the scope of this genus, the compound must (1) be a barbituric acid chemical derivative, (2) not be sedating, in the sense that the subject remains awake and alert at useful doses, that is, not anesthetized, and (3) manifest neuroprotective activity in an animal model described herein or in a human at a dose that is not toxic to the relevant animal species, or show activity in an in vitro assay now known or later discovered that is accepted as a model for in vivo neuroprotection.

These barbituric acid derivatives may be both prodrugs and active ingredients in the subject, thus combining to produce the desired pharmacodynamic effect of neuroprotection. Sustained levels are readily obtained with such compounds.

Thus, certain barbiturate compounds have been developed and have anticonvulsant activity without being sedating even at very high brain concentrations (that would be lethal with other barbiturates). According to the invention, such compounds are used to neuroprotect an animal at risk for or suffering from one or more ischemic episodes such as that modeled by middle cerebral artery occlusion, while these compounds do not cause the toxic effects of other barbiturates when present at concentrations required for prevention of ischemic brain damage.

As described herein, non-sedative barbiturate drugs lessen or prevent ischemic brain damage in a rat model of focal cerebral ischemia produced by middle cerebral artery occlusion. This demonstrates utility in humans.

In a reproducible, predictive model of cerebral ischemia known in the art, selective neuronal damage is produced in the striatum and cerebral cortex by bilateral carotid occlusion accompanied by systemic hypotension. The resulting cerebral ischemia causes a release of excitotoxic neurotransmitters and dopamine in striatum. Pentobarbital inhibited this ischemia-induced release, pointing to one possible mechanism of barbiturate neuroprotection. (5) A neuroprotective dose of pentobarbital was found to be 70 mg/kg. Inhibition of neurotransmitter release by several neuroprotective anesthetic agents (isoflurane, etomidate, propofol) was also known.

The above and similar animal models (see Examples) can be used (1) to analyze whether a non-sedative barbiturate with anticonvulsant properties but little or no anesthetic activity can provide neuroprotection in the striatum or hippocampus, and (2) to determine if the agent prevents or reduces release of neurotransmitters in response to ischemia. Uncontrolled or unmodulated neurotransmitter release is one of the postulated mechanism of ischemic damage. For non-sedating barbiturates that inhibit release of neurotransmitters, this approach can serve as a biochemical assay for predicting utility of a compound according to the invention, and the invention encompasses such methods.

A neuroprotective effect according to the invention can be demonstrated and characterized by performing a dose-response study and measuring statistically significant differences in neuronal damage at the various doses of the drug. Dose-response curves generated in such studies can be used to compare the relative degree of neuroprotection and sedation of a test compound.

Cerebral ischemia is induced in rats by occlusion of the middle cerebral artery ("MCA") (7-9). The occlusion can be performed in an irreversible or reversible manner. In the latter case, after a period of obstruction, blood flow is restored. These animal preparations are thus appropriate to model various types of strokes in humans and to permit determination of a drug's neuroprotective action. Such models permit observation of the prevention of brain damage and the evaluation of the drugs as being useful for humans who are at risk for ischemic stroke for reduction of subsequent brain damage induced by an ischemia event. Because they prevent brain damage in models of irreversible ischemia and reversible ischemia with restoration of blood flow, the compounds of the invention are also useful for treating acute ischemic stroke either alone or in combination with other agents, for example, thrombolysins such as tissue plasminogen activator that reduce the extent of brain infarction when circulation is restored.

The term "treatment" is intended to encompass administration of compounds according to the invention prophylactically to prevent or suppress an undesired condition, and therapeutically to eliminate or reduce the extent or symptoms of the condition. Treatment according to the invention is given to a human or other mammal having a disease or condition creating a need of such treatment. Treatment also includes application of the compound to cells or organs in vitro. Treatment may be by systemic or local administration.

The non-sedative barbiturate compositions of the present invention, may be formulated into "pharmaceutical compositions" with appropriate pharmaceutically acceptable carriers, excipients or diluents. If appropriate, pharmaceutical compositions may be formulated into preparations including, but not limited to, solid, semi-solid, liquid, or gaseous forms, such as tablets, capsules, powders, granules, ointments, solutions, suppositories, injections, inhalants, and aerosols, in the usual ways for their respective route of administration.

Methods known in the art can be used to achieve time-release of the composition or to prevent metabolism, release or absorption of the composition until it has reached its intended target site. A pharmaceutically-acceptable formulation should be employed that does not inactivate the active drug of the present invention.

In pharmaceutical dosage forms, the compositions may be used alone or in appropriate association, as well as in combination with, other pharmaceutically-active compounds.

The pharmaceutical compositions of the present invention can be delivered via various routes and to various sites in an animal body to achieve the desired neuroprotective effect.

Local or systemic delivery can be accomplished by injection, infusion, application or instillation of the composition into one or more body cavities, or by inhalation or insufflation of an aerosol. Parenteral administration can be by intramuscular, intravenous, intraperitoneal, subcutaneous intradermal, or topical administration.

The compositions of the present invention can be provided in unit dosage form, wherein each dosage unit, e.g., a teaspoon, tablet, solution, or suppository, contains a predetermined amount of the active drug or prodrug, alone or in appropriate combination with other pharmaceutically-active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically-acceptable diluent, carrier (e.g., liquid carrier such as a saline solution, a buffer solution, or other physiological aqueous solution), or vehicle, where appropriate. The specifications for the novel unit dosage forms of the present invention depend on the particular effect to be achieved and the drug's particular pharmacodynamics in the particular host.

An "effective amount" of the composition is that required to produce the desired pharmacologic effect in a host. This can be monitored using any of a number of end-points known to those skilled in the art. The "effective dose" will depend on the bioavailability of specific dosage forms delivered by one or another route of administration. The neuroprotective dosage and blood level of the present compounds is at least 2-fold and preferably at least about 5 to 10-fold the anticonvulsant dosage of a sedating barbiturate. Based on rat data, the anticonvulsant $ED_{50}$ for phenobarbitol is about 50-100 mg/kg. A non-sedating barbiturate dose of 1 g/kg given over 7 days protects against cerebral ischemia in the rat. Similar or lower doses are suitable in humans based on the enhanced absorption in humans discussed above.

The amount of each active agent employed in the Examples below provides general guidance for the range that can be utilized by the skilled practitioner to optimize the doses and methods of the present invention. Moreover, such dose ranges do not preclude use of a higher or lower dose of a component, as might be warranted in a particular application. For example, the actual dose and schedule may vary depending on whether the compositions are administered in combination with other drugs, or depending on inter-individual differences in pharmacokinetics, drug disposition, and metabolism. Similarly, amounts may vary for in vitro applications. It is within the skill in the art to readily adjust the dose in accordance with the necessities of a particular situation without undue experimentation Having now generally described the invention, the same will be more readily understood through reference to the following examples which are provided by way of illustration, and are not intended to be limiting of the present invention, unless specified.

EXAMPLE 1

General Design

The non-sedative barbiturate (NSB) drug is tested in rats exposed to either reversible or irreversible ischemia. Varying doses of drug are administered. The neuroprotective effect is compared to a negative control (placebo) and a positive control, pentobarbital, a known neuroprotective but sedative barbiturate, given at doses known to reduce infarct volume in cerebral ischemia (1-4).

Animals are sacrificed several days after the onset of the ischemic insult and the brains examined to determine the volume of brain infarction as an outcome measure of the drug's reduction of ischemic brain damage. The animals are examined clinically and graded prior to sacrifice to determine if the drug has conferred any beneficial effect on relevant functions following ischemic "stroke."

Four experimental models are preferred for testing the neuroprotective effects of the NSB drug. See Ginsberg, M. D., "Animal Models of Global and Focal Cerebral Ischemia," Chapter 34 in Welsh, K. M. A et al., *Primer on Cerebrovascular Diseases*, Academic Press, New York, 1997; and Pulsinelli W A, Brierley J B. A new model of bilateral hemispheric ischemia in the unanesthetized rat, Stroke 1979 May-June 10(3): 267-72.

1. Irreversible ischemia produced by middle cerebral artery (MCA) occlusion;
2. Reversible ischemia produced by MCA occlusion;
3. Transient global ischemia produced by cross-clamping the aorta for a defined interval; and
4. Transient global ischemia produced by cauterizing both vertebral arteries and reversibly clamping the common carotid arteries.

In each experimental model, groups of rats are treated with either:

1. Negative control (placebo) via nasogastric (NG) tube;
2. Positive control: intraperitoneal (IP) dose of 70 mg/kg pentobarbital; or
3. The NSB compound DMMDPB (or a compound being tested for its utility in the present invention) via NG tube at doses between 500 mg/kg and 1500 mg/kg for 7 days prior to experimental infarctions.

The results are compared.

EXAMPLE 2

Irreversible Cerebral Ischemia

Irreversible MCA occlusion was produced by ligating the carotid artery and then inserting a filament into the origin of the MCA with the animal maintained under halothane anesthesia. Blood flow in the MCA was measured by laser doppler and those animals in which a significant drop in blood flow occurred were considered to have experienced cerebral ischemia, and to be at risk for subsequent damage (i.e., a stroke). Indeed, no clinical strokes occurred in animals that did not experience a precipitous drop in MCA blood flow. All the animals showing with a drop in MCA blood flow experienced strokes.

Animals at risk were then followed behaviorally and scored by clinical findings using the Bederson grading scale as either:

0 no evidence of stroke
1 mild stroke
2 moderate stroke
3 severe stroke

Those animals that survived for three days were sacrificed and their brains examined. Animals to be sacrificed were given chloral hydrate (35 mg/kg IP, and their brains were fixed by intracardiac perfusion with heparinized 0.9% saline followed by 10% buffered formalin. The brains were removed from the cranial vault with care to leave the arachnoid intact with the intracranial vessels underneath. The fixed brains were frozen at 80° C. Coronal sections 20 μm thick were cut at 400 μm intervals in a cryostat at −20° C., dried on a hot plate at 60° C., fixed in 90% ethanol for 10 minutes and stained with hematoxylin and eosin (7). Infarcted brain is pale compared to the rest of the brain. The amount of infarcted brain was determined by microscopic inspection of the brain sections and calculation of infarct volumes in $mm^3$.

The results are shown in Tables 1 and 2 below. The numbers vary between groups because not all animals experienced a drop in MCA blood flow with the procedure. All animals were treated with DMMDPB dosages of 1000 mg/kg/day for 7 days.

TABLE 1

Effect of DMMDPB on Death due to Cerebral Ischemia

| Treatment Group | Behavior | n | Death within 24 hr | Survival at 24 hr n (%) | Survival at 48 hr n (%) | Survival at 72 hr n (%) |
|---|---|---|---|---|---|---|
| Control (males) | Sedated | 12 | 9 (75%) | 3 (25%) | 2 (17%) | 1 (8%) |
| Pentobarbital (males) | Sedated | 9 | 6 (67%) | 3 (33%) | 3 (33%) | 3 (33%) |
| DMMDPB | Not sedated | 17 | 2 (12%) | 15 (88%) | 10 (59%) | 8 (47%) |
| Males | | 14 | 2 (24%) | 12 (76%) | 7 (50%) | 5 (36%) |
| Females | | 3 | 0 (0%) | 3 (100%) | 3 (100%) | 3 (100%) |

Other dose ranging studies in rats treated with DMMDPB for 7 days established that female rats have substantially higher blood levels than male rats. Specifically, at a dosage of DMMDPB of 500 mg/kg the total barbiturate level in males was 59 μg/ml and females 170 μg/ml. At a dosage of 1000 mg/kg the total barbiturate level in males was 77 μg/ml and females 227 μg/ml; and at a dosage of 2000 mg/kg the total barbiturate level in males was 110 μg/ml and females 328 μg/ml. Thus females consistently had blood levels 250%-300% that of males at the same dosage. This data shows a type of "dose response effect" or "blood level response effect" whereby higher blood levels correlate to higher survival in female rats in the results tabulated above.

TABLE 2

Neurologic status of the first 9 animals of Table 1

| Treatment group | Rat# | Weight (g) | Neurologic Status (Bederson grading scale 0-3) | | | Pathology |
| | | | Day 1 | Day 2 | Day 3 | |
|---|---|---|---|---|---|---|
| Placebo | 1 | 260 | 3 | X | | Died 24 hrs |
| | 2 | 260 | 3 | X | | Died 24 hrs |
| | 3 | 240 | 3 | X | | Died 24 hrs |
| Pentobarbitol | 1 | 260 | 0 | 1 | 1 | SAH (autopsy) |
| | 2 | 250 | 2 | 2 | 2 | Brain collected |
| DMMDPB | 1 | 270 | 1 | 1 | 1 | Brain collected |
| | 2 | 230 | 3 | 3 | X | Died 48 hrs |
| | 3 | 240 | 2-3 | 3 | X | Died 48 hrs |
| | 4 | 260 | 2-3 | 3 | 3 | Brain collected |

Pathology (visual and microscopic examination) shows smaller infarct volumes in animals pretreated with pentobarbitol and DMMDPB.

Thus, DMMDPB proved to protect the animals against death. Other data indicated that DMMDPB treated animals did not manifest sedation compared to placebo group. In contract, the pentobarbital animals were anesthetized and immobile. The neuroprotective effects at non-sedating doses were comparable to or better than the effects of the sedative pentobarbital but without the side effects-of sedation, particularly at day two.

These neuroprotective effects of DMMDPB are predictive for monomethoxymethyl diphenyl barbituric acid (MMMDPB) and the presumptive pharmacologically active chemical moiety diphenyl barbituric acid (DPB), which are metabolic products of DMMDPB. Indeed, in animal studies over periods ranging from 1-30 days DMMDPB was rapidly metabolized to MMMDPB and eventually to DPB.

Results from clinical studies with humans demonstrated a pattern of blood levels similar to that seen in animals: DPB>MMMDPB>DMMDPB. Again, the same pattern was shown in that blood levels of DMMDPB were minimal, while MMMDPB and DPB concentration was higher. This animal model of neuroprotection is predictive for humans because: (a) the metabolic behavior of this compound in animals is predictive of human metabolism, and (b) the anticonvulsant activity in animals correlates with anticonvulsant activity in humans.

Although several sedative barbituric compounds previously found to be neuroprotective in such animal models provided some benefit in human studies, their use over even relatively short time periods is precluded by their sedative and other neurological and psychological side-effects. These side effects make prophylactic treatment infeasible for patients identified as being at high risk of stroke. According to the present invention, in contrast, the NSBs have minimal side effects in humans. Thus, it is now established that diphenyl barbituric acid and its precursors, analogues and derivatives constitute a class or family of compounds suitable for neuroprotection of humans.

EXAMPLE 3

Reversible Cerebral Ischemia Model

Rats are pretreated as in Example 1 (above) and a similar procedure is performed except that the filament occluding the MCA is removed after 30 to 60 minutes, restoring blood flow through the MCA. Rats are then followed clinically for three days, graded for their degree of stroke and then sacrificed as in Example. The brains are removed and examined as described above.

The NSB compounds are shown to be neuroprotective under these conditions.

EXAMPLE 4

Rats are pretreated as in Example 1 (above) and then, during ether anesthesia, the rats' vertebral arteries are electrocauterized through the alar foramina of the first cervical vertebra. Reversible clamps are then placed loosely around the common carotid arteries. After 24 hours, working with awake rats, the carotid clasps are tightened to produce 4-vessel occlusion. Following 10-30 minutes of 4-vessel occlusion, the clasps are removed and 72 hours later the animals sacrificed by perfusion fixation. Untreated rats routinely demonstrate ischemic neuronal damage after 20 or 30 minutes of 4-vessel occlusion. Multiple areas of the forebrain, including the H1 and paramedian hippocampus, striatum, and posterior neocortex are evaluated. The non-sedating barbiturates are shown to be neuroprotective under these circumstances.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

REFERENCES

1. Hoff J T, Smith A L, Hankinson H L, Nielsen S L. Barbiturate protection from cerebral infarction in primates. Stroke 1975; 6:28-33
2. Levy D E, Brierley J B. Delayed pentobarbital administration limits ischemia brain damage in gerbils.
3. Lightfoote W E II, Molinari G F, Chase T N. Modification of cerebral ischemia damage by anesthetics. Stroke 1977; 8:627-628
4. Corkill G, Chikovani O K, McLeish I, McDonald L W, Youmans J R. Timing of pentobarbital administration for brain protection in experimental stroke. Surg Neurol 1976; 147-149
5. Bhardwaj A, Brannan T, Weinberger J. Pentobarbital inhibits extracellular release of dopamine in the ischemia striatum. J Neural Transom 1990; 82: 111-117
6. Masuda Y, Utsui Y, Shiraishi Y, Karasawa T, Yoshida K, Shimizu M. Relationships between plasma concentrations of diphenylhydantoin, phenobarbital, carbarnapezine, and 3-sulfmoylmethyl-1,2-benzisoxazole (AD-810), a new anticonvulsant agent, and their anticonvulsant or neurotoxic effects in experimental animals. Epilepsia 1979; 20:623-633
7. Brint S B, -Jacewicz M, Kiessling M, Tanabe J, Pulsinelli W. Focal brain ischemia in the rat: Methods for reproducible neocortical infarction using tandem occlusion of the distal middle cerebral and ipsilateral common carotid arteries. J Cerebral Blood Flow Metab 1988; 8:474-485
8. Garcia J H, Wagner S, Liu K-F, Hu X-j. Neurological deficit and extent of neuronal necrosis attributable to middle cerebral artery occlusion in rats. Statistical validation. Stroke 1995; 26:627-634
9. Garcia J H, Liu K-F, Ho K-L. Neuronal necrosis after middle cerebral artery occlusion in Wistar rats progresses at different time intervals in the caudoputamen and the cortex. Stroke 1995-26:636-643.
10. Stroke Therapy: Basic clinical and pre-clinical directions, Leonard P. Miller, ed. (Wiley 1999).
11. Ginsberg, M. D., Animal Models of Global and Focal Cerebral Ischemia, Chapter 34 in Eds. Welsh, K. M. A, Caplan, L. R., Reis, P. J., et al, Primer on Cerebrovascular Diseases, Academic Press 1997.
12. Pulsinelli W A, Brierley J B. A new model of bilateral hemispheric ischemia in the unanesthetized rat, Stroke 1979 May-June 10(3): 267-72
13. Pulsinelli, W A, Brierly J B, Plum F. Temporal Profile of neuronal damage in a model of transient forebrain ischemia, Annals of Neurology, 1982, May, 11(5) 491-8.

What is claimed is:

1. A method for providing neuroprotection to a human in need thereof comprising, administering a therapeutically effective amount of a pharmaceutical composition of a salt of 5,5-diphenyl barbituric acid to the human, wherein the human is undergoing cardiac surgery or carotid endarterectomy, or has had an atrial fibrillation, transient ischemic attacks (TIAs), bacterial endocarditis, ischemic stroke, or subarachnoid hemorrhage due to a cerebral aneurysm.

2. The method of claim 1 wherein, the pharmaceutical composition of the salt of diphenyl barbituric acid is administered orally.

3. The method of claim 2 wherein, the pharmaceutical composition is administered parenterally.

4. The method of claim 3 wherein, the pharmaceutical composition is administered intravenously.

5. The method of claim 1 wherein, the pharmaceutical composition is a solid.

6. The method of claim 1 wherein, the pharmaceutical composition is a liquid.

7. The method of claim 1 wherein, greater than about 50 mg/kg of body weight of the pharmaceutical composition of the salt of diphenyl barbituric acid is administered.

8. The method of claim 1 wherein, greater than about 70 mg/kg of body weight of the pharmaceutical composition of the salt of diphenyl barbituric is administered.

9. The method of claim 1 wherein, greater than about 100 mg/kg of body weight of the pharmaceutical composition of the salt of diphenyl barbituric is administered.

10. The method of claim 1 wherein, greater than about 250 mg/kg of body weight of the pharmaceutical composition of the salt of diphenyl barbituric is administered.

11. The method of claim 1 wherein, greater than about 500 mg/kg of body weight of the pharmaceutical composition of the salt of diphenyl barbituric acid is administered.

12. The method of claim 1 wherein, greater than about 1000 mg/kg of body weight of the pharmaceutical composition of the salt of diphenyl barbituric acid is administered.

13. A method of administering a therapeutically effective amount for providing neuroprotection to a human in need thereof of a pharmaceutical composition of a salt of 5,5-diphenyl barbituric acid, comprising administering to the human a salt of 5,5-diphenyl barbituric acid in a quantity sufficient to produce blood concentrations of 5,5-diphenyl barbituric acid or an active metabolite thereof of at least about 30 µg/ml in the human, wherein the human is undergoing cardiac surgery or carotid endartectomy, or has had an atrial fibrillation, transient ischemic attacks (TIAs), bacterial endocarditis, ischemic stroke, or subarachnoid hemorrhage due to a cerebral aneurysm.

14. The method of claim 13 wherein, the amount of the pharmaceutical composition of the salt of diphenyl barbituric acid administered is sufficient to produce blood concentrations of diphenyl barbituric acid or an active metabolite of at least about 50 µg/ml.

15. The method of claim 14 wherein, the amount of the pharmaceutical composition of the salt of diphenyl barbituric acid administered is sufficient to produce blood concentrations of diphenyl barbituric acid or an active metabolite of at least about 100 µg/ml.

16. The method of claim 15, wherein the amount of the pharmaceutical composition of the salt of diphenyl barbituric acid administered is sufficient to produce blood concentrations of diphenyl barbituric acid or an active metabolite of at least about 1000 µg/ml.

17. A method of providing a neuroprotectant to a human comprising administering a therapeutically effective amount of a pharmaceutical composition of a salt of 5,5-diphenyl barbituric acid to the human, wherein the human is undergoing cardiac surgery or carotid endarterectomy, or has experienced cerebral ischemia, a cerebral aneurysm, or head trauma, and is at risk for atrial fibrillation, transient ischemic attack (TIA), bacterial endocarditis, ischemic stroke, head trauma or subarachnoid hemorrhage.

18. The method of claim 17 wherein, the pharmaceutical composition is administered orally.

19. The method of claim 18 wherein, the pharmaceutical composition is administered parenterally.

20. The method of claim 19 wherein, the pharmaceutical composition is administered intravenously.

21. The method of claim 17 wherein, the pharmaceutical composition is a solid.

22. The method of claim 17 wherein, the pharmaceutical composition is a liquid.

23. The method of claim 1, wherein the compound is administered before onset of neuronal damage.

24. The method of claim 1, wherein the compound is administered therapeutically after onset of neuronal damage.

25. The method of claim 1, wherein the neuroprotective effect diminishes, or protects the subject from, neuronal damage caused by head trauma or cerebral ischemia.

26. The method of claim 1, where the compound is administered in conjunction with cardiac surgery or carotid endarterectomy.

27. The method of claim 1, wherein the human has had an atrial fibrillation, a transient ischemic attack (TIA), bacterial endocarditis, an ischemic stroke or subarachnoid hemorrhage.

* * * * *